(12) United States Patent
Nair et al.

(10) Patent No.: US 7,335,804 B2
(45) Date of Patent: Feb. 26, 2008

(54) DIRECT CONVERSION OF HCFC 225CA/CB MIXTURE

(75) Inventors: Haridasan Nair, Williamsville, NY (US); Sudip Mukhopadhyay, Buffalo, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 22 days.

(21) Appl. No.: 11/265,949

(22) Filed: Nov. 3, 2005

(65) Prior Publication Data

US 2007/0096053 A1    May 3, 2007

(51) Int. Cl.
  *C07C 19/08*    (2006.01)
(52) U.S. Cl. .................. 570/134; 570/170; 570/176
(58) Field of Classification Search ............ 570/134, 570/170, 176
  See application file for complete search history.

(56) References Cited

U.S. PATENT DOCUMENTS

| 2,931,840 | A |   | 4/1960 | Marquis ................. 260/653.3 |
| 2,996,555 | A |   | 8/1961 | Rausch ................... 260/653.4 |
| 5,421,971 | A |   | 6/1995 | Van Der Puy et al. .. 204/157.6 |
| 5,430,206 | A | * | 7/1995 | Merchant et al. ........... 570/178 |
| 5,532,418 | A |   | 7/1996 | Nakada et al. .............. 570/166 |
| 5,663,543 | A |   | 9/1997 | Morikawa et al. ....... 204/157.6 |
| 5,756,869 | A | * | 5/1998 | Yoshikawa et al. ......... 570/176 |
| 5,856,594 | A | * | 1/1999 | Thenappan et al. ......... 570/176 |
| 6,184,426 | B1 |  | 2/2001 | Belen'Kill et al. ......... 570/172 |
| 7,026,520 | B1 | * | 4/2006 | Mukhopadhyay et al. .. 570/123 |

FOREIGN PATENT DOCUMENTS

| EP | 0 328 148 | 2/1989 |
| JP | WO9008753 | 9/1990 |
| JP | WO 94/05611 | 3/1994 |
| JP | WO 95/06629 | 3/1995 |

OTHER PUBLICATIONS

Programme for Alternative Fluorocarbon Toxicity Testing, *HFC-225$^{ea}$/cb*, Sep. 1995.

\* cited by examiner

*Primary Examiner*—John R. Hardee
(74) *Attorney, Agent, or Firm*—Colleen D. Szuch

(57) ABSTRACT

Provided are methods for producing hydrofluorocarbons via the selective reduction of a halocarbon blend comprising 1,3-dichloro-1,1,2,2,3-pentafluoropropane.

39 Claims, No Drawings

DIRECT CONVERSION OF HCFC 225CA/CB MIXTURE

BACKGROUND

1. Field of Invention

The present invention is directed to methods for selectively reacting halocarbon isomers and to methods of selectively removing one or more halocarbon isomers from blends containing multiple isomeric forms. More particularly, the invention is directed to methods for the selectively reducing a halocarbon blend comprising 1,3-dichloro-1,1,2,2,3-pentafluoropropane. More specifically, the invention relates to methods for preparing hydrofluorocarbons via the selective reduction of a halocarbon blend comprising 1,3-dichloro-1,1,2,2,3-pentafluoropropane.

2. Description of Related Art

Many halocarbons, particularly lower halocarbons, find use in a variety of applications, including refrigerants, propellant gases, fire-extinguishing agents, blowing agents for foams, and many others. As used herein, the term "halocarbon" means a compound containing carbon, one or more halogens, and optionally hydrogen. Halocarbons of particular interest with respect to the present invention are "C3 halocarbons," that is, halocarbons having three (3) carbon atoms in the chain, including C3 hydrochlorofluorocarbons, C3 hydrofluorocarbons, and C3 hydrofluoroolefins.

Exemplary of such compounds are $CF_3CF_2CHCl_2$ (HCFC-225ca), $CClF_2CF_2CHClF$ (HCFC-225cb), $CF_3CF_2CH_2Cl$ (HCFC-235ca), $CF_3CF_2CH_3$ (HFC-245cb), $CF_3CFHCH_3$ (HFC-254 eb), and $CF_3CF=CH_2$ (HFO-1234yf).

Applicants have also come to appreciate the need safe and effective starting materials for the production of certain C3 halocarbons, particularly C3 fluoroolefins. For example, applicants have come to appreciate the advantage of providing inexpensive feedstock for the production of relatively non-toxic, environmentally acceptable, and useful C3 halocarbons, such as trifluoropropenes (e.g., $CF_3CH=CH_2$ (HFC-1243zf)), tetrafluoropropenes (e.g., $CF_3CF=CH_2$ (HFC-1234yf)), pentafluoropropene (e.g., $CF_3CF=CFH$ (HFC 1225 ye)), and the like. Other C3 halocarbons which can be produced include $HCF_2CF_2CH_3$, $CF_3CF_2CH_2Cl$ (HCFC 235ca), $CF_3CF_2CH_3$ (HFC-245cb) and the like.

HCFC-225ca and HCFC-225cb are two isomers of dichloropentafluoropropane that have been proposed as alternatives to trichlorotrifluoroethane (CFC-113) for use as a cleaning solvent. CFC-113 is undesirable for use in many applications because it is considered to be environmentally unfriendly. HCFC-225ca and HCFC-225cb are known to be easily and economically obtained by the reaction of dichlorofluoromethane and tetrafluoroethylene. Blends of these HCFC-225 isomers have been commercialized. For example, Asahi Glass Co. of Japan markets a 47/53 weight percent blend of HCFC-225ca/cb under the name Asahiklin AK-225.

Applicant's have come to recognize the existence of toxicity studies indicating that both HCFC-225ca and HCFC-225-cb have very low acute toxicity compared to CFC-113. [See e.g. PAFT HCFC-225ca/cb Testing Web Site (www.afeas.org/paft/hcfc-225.html) showing that CFC-113 has a cardiac sensitization response three times that of HCFC-225ca/HCFC-225cb blends]. Even though both of these dichlorotetrafluoropropane isomers have a relatively low level of toxicity, applicant's have further recognized that HCFC-225ca nevertheless has been found to be significantly more toxic than HCFC-225cb. For example, PAFT testing has shown that an HCFC-225ca exposure level of 650 to 1000 ppm had a substantially greater effect on the liver of the animal in comparison to HCFC-225cb, which at even greater exposure levels of 1000 to 5000 ppm had only marginal effects. Moreover, the US Environmental Protection Agency has set an average workplace standard exposure level of 250 ppm for the cb isomer, but only 25 ppm for the ca isomer. (See e.g. US EPA "Substitutes in Precision Cleaning" at www.epa.gov/ozone/snap/solvents/lists/precisio.html.)

In general, it is preferable to minimize workplace exposure to toxic chemicals. In a mixture or blend of compounds that may potentially be exposed to humans or other animals, for example during use, transportation and the like, it is generally therefore less of a disadvantage from a toxicity standpoint for the blend or mixture to contain HCFC-225cb than for it to contain a like amount of HCFC-225ca.

Reactions involving the conversion of chlorofluoropropanes, such as HCFC-225ca and/or HCFC-225cb, are known. For example, U.S. Pat. No. 5,663,543 (Morikawa) describes the oxidation of at least one dichloropentafluoropropane selected from HCFC-225ca and HCFC-225cb by oxygen under irradiation with and in the presence of chlorine. The product resulting from this reaction is a polyfluoropropionyl halide. Another example of such conversion can be found in U.S. Pat. No. 5,532,418 (Nakada) which teaches a method for producing a hexafluoropropane via a multi-step process whereby HCFC-225ca and/or HCFC-225cb is de-chlorofluorinated by hydrogen in the presence of a metal oxide catalyst to obtain a tetrafluorochloropropene, which is subsequently fluorinated to produce hexafluoropropane.

However, neither Morikawa nor Nakada teach or even suggest the selective conversion of HCFC-225ca over HCFC-225cb. In fact, Nakada actually teaches that under the reaction conditions specified therein HCFC-225cb is more readily converted to other compounds than HCFC-225ca. In addition, neither of these patents teach or suggest direct synthesis of a hydrofluorocarbon or hydrofluoroolefin from a dichloropentafluoropropane or blend of dichloropentafluoropropane isomers

SUMMARY OF THE INVENTION

In view of the above, applicants have discovered advantageous methods and/or means of converting halocarbon blends containing HCFC-225ca, particularly isomeric blends of HCFC-225ca and HCFC-225cb, into a composition comprising HCFC-225cb, but having little or no HCFC-225ca. In this way, one embodiment of the present invention provides a method of purifying a mixture comprising HCFC-225ca and HCFC-225cb so as to remove a substantial portion of the HCFC-225ca, and preferably substantially all of the HCFC-225a, to produce a composition in which the weight ratio of HCFC-225cb:HCFC-225cb is relatively high, preferably greater than 2:1, even more preferably greater than 4:1, and even more preferably greater than about 10:1. In certain preferred embodiments, the mixture to be purified consists essentially of HCFC-225cb and HCFC-225ca.

Applicants have also found that it would be advantageous to selectively convert relatively inexpensive blends of HCFC-225ca/cb into compositions containing compounds such as hydrofluorocarbons, hydrochlorofluorocarbons, and/or hydrofluoroolefins, preferably C3 hydrofluorocarbons, C3 hydrochlorofluorocarbons and/or C3 hydrofluoroolefins. In certain preferred embodiments, the conversion step, which preferably comprises reduction, produces C3 hydrofluorocarbons including pentafluorinated C3 hydrofluorocarbons, such as $CF_3CF_2CH_3$ (HFC-245cb), and tetrafluorinated C3 hydrofluorocarbons, such as $HCF_2CF_2CH_3$. In certain preferred embodiments, the preferred conversion step produces C3 hydrofluoroolefins, including tri, tetra and penta-fluorinated C3 hydrofluoroolefins, for example the trifluorinated olefin $CF_3CH=CH_2$, the tetra-fluorinated olefin, $CF_3CF=CH_2$ (HFC-1234yf) and the penta-fluorinated olefin $CF_3CF=CFH$(HFC 1225 ye). In other preferred embodiments, the conversion step produces C3 hydrochlorofluorocarbons such as $CF_3CF_2CH_2Cl$ (HCFC 235cb).

One aspect of the present invention is thus directed to methods of reducing one or more halocarbon compounds from a halocarbon blend comprising HCFC-225cb. Specifically, applicants have discovered that the dichloropentafluoropropane isomer HCFC-225cb is not substantially reduced under reaction conditions that would normally lead to the reduction of halocarbons, such as dichloropentafluoropropanes other than HCFC-225cb. This discovery can be advantageously used to selectively reduce certain halocarbons, particularly dichloropentafluoropropane isomers other than HCFC-225cb, in blends comprising HCFC-225cb. Moreover, as described above, it may be desirable in some instances to utilize this discovery to form a relatively high purity HCFC-225cb.

Thus one aspect of the present invention is an advantageous method of preparing hydrofluorocarbons directly from a halocarbon blend comprising HCFC-225cb, and even more preferably from a blend comprising HCFC-225cb and HCFC-225ca. Preferably the methods are carried out without converting any substantial amount of said HCFC-225cb to other compounds. In particular embodiments, the methods comprise the steps of: (a) providing a halocarbon blend comprising 1,3-dichloro-1,1,2,2,3-pentafluoropropane (HCFC-225cb) and at least one other halocarbon which is not a hydrofluorocarbon; and (b) contacting said blend with a reducing agent under conditions effective to convert at least a substantial portion of said at least one other halocarbon to at least one hydrofluorocarbon. In certain preferred embodiments the other halocarbon is a C3 HCFC, preferably HCFC-225cb, and the one hydrofluorocarbon preferably comprises at least one C3 hydrofluoroolefin, preferably at least one tetrafluoropropene, and even more preferably $CF_3CF=CH_2$ (HFO-1234yf).

Another aspect of the present invention is a method for selectively reducing one or more compounds in a halocarbon blend comprising HCFC-225cb. Such selective reduction can be used to convert certain relatively toxic halocarbon compositions, including compositions containing compounds that are more toxic than HCFC-225cb (such as HCFC-225ca), into compositions which are overall less toxic than the starting composition. In addition, this method can produce certain desirable compounds such as chlorine- and/or fluorine-substituted aliphatics, including for example, hydrochlorofluorocarbons, hydrofluorocarbon, and fluorine substituted olefins, preferably hydrofluoroolefins, and the like. In particular embodiments, the methods preferably comprise the steps of (a) providing a halocarbon blend comprising HCFC-225cb at least one other halocarbon which is not a hydrofluorocarbon; and (b) contacting said blend with a reducing agent to reduce at least a portion of said other halocarbon, wherein a majority of said HCFC-225cb is not reduced, and preferably more than about 90 percent by weight of said HCFC-225cb is not reduced.

DETAILED DESCRIPTION OF THE INVENTION

The term "blend", as used herein, means a combination of at least two substances, which may or may not be uniform. In preferred embodiments, either of the two substances preferably could be used alone for a purpose that is the same as or similar to that of the blend. For example, preferred blends of the present invention can include mixtures of two or more halogen substituted compounds such as hydrochlorofluorocarbons, chlorofluorocarbons, hydrofluorocarbons, fluorocarbons, hydrofluoroolefins, and the like.

Preferred blends according to the present invention are those including the compound HCFC-225cb. More preferred are blends comprising HCFC-225cb and at least one other hydrochlorofluorocarbon that can be reduced in the presence of a reducing agent, such as hydrogen. Even more preferred are blends comprising two or more isomers of dichloropentafluoropropane, at least one of which is HCFC-225cb. In certain preferred embodiments, the blend will comprise HCFC-225ca and HCFC-225cb, and in certain other preferred embodiments the blend consists essentially of HCFC-225ca and HCFC-225cb. In still other preferred embodiments, the blend consists essentially of from about 1 to about 99 weight percent HCFC-225cb (more preferably from about 40 to about 55 weight percent of HCFC-225cb) and from about 1 to about 99 weight percent HCFC-225ca (more preferably from about 45 to about 60 weight percent of HCFC-225ca).

As used herein, the term "reduction" generally means a chemical reaction wherein hydrogen is added to a compound, preferably by substituting the hydrogen for a halogen. In preferred embodiments the halogen which is substituted in the reduction step is chlorine. In certain preferred embodiments, therefore, the reduction step also involves at least a partial dehalogenation of the compound, which preferably includes at least a partial dechlorination of the compound, and more preferably complete dechlorination of the compound.

Applicants have unexpectedly discovered that conditions which are effective to reduce many halocarbons, particularly HCFC-225ca, are not particularly effective to reduce, and preferably do not substantially reduce, HCFC-225cb. By the phrase "not substantially reduced", it is meant that under conditions effective to reduce dichloropentafluoropropane isomers other than HCFC-225cb, such other isomers are, or would likely be, reduced at a rate of at least about 2:1 compared to the reduction rate of HCFC-225cb. (That is, for example, if 50:50 blend of HCFC-225ca/cb were subjected to reduction conditions in accordance with preferred aspects of the present invention, HCFC-225ca would be reduced at least twice as readily as HCFC-225cb.) In highly preferred embodiments, the other halocarbon, and particularly HCFC-225ca, is reduced at a rate of at least about 5:1, and even more preferably of at least about 10:1, compared to the reduction rate of HCFC-225cb. In certain preferred embodiments, not more than about 10% of the HCFC-225cb, and even more preferably not more than about 5% of the HCFC-225cb, present in blend is reduced as a result of the reduction step.

This discovery, therefore, can be used to selectively reduce certain halocarbons in a blend comprising HCFC-225cb, including blends comprises other dichloropentafluoropropane isomers. By way of a non-limiting example, the HCFC-225ca in a blend of HCFC-225ca/cb can be reduced according to the present invention to form hydrochlorofluoropropanes, hydrofluoropropanes, and hydrofluoropropenes, such as those described above.

Preferred reducing agents for use with the present invention include hydrogen gas and/or ammonium formate.

In certain preferred embodiments, the reducing agent is used in presence of a catalytic amount of a catalyst such as, for example, palladium on carbon or tetrakis(triphenylphosphine) palladium. Other suitable catalysts can be can be found in reference *Catalytic Hydrogenation-Techniques and Applications in Organic Synthesis* by R. L. Augustine, 1965, Marcel Deeker Inc. New York, which is incorporated herein by reference. Preferably, embodiments that utilize hydrogen gas as a reducing agent will also utilize a catalytic amount of palladium on carbon, and embodiments that utilize ammonium formate will also utilize a catalytic amount of tetrakis(triphenylphosphine) palladium.

Also, in certain preferred embodiments, the reducing agent is used in the presence of a solvent, such as for example, a lower alcohol (methanol, ethanol, and the like) or tetrahydrofuran (THF). Preferably, embodiments that utilize hydrogen gas as a reducing agent will also utilize methanol or ethanol as a solvent. In embodiments that utilize ammonium formate as a reducing agent will preferably utilize THF as a solvent.

In certain embodiments, the method is performed as a batch process, preferably in an autoclave at a temperature of from about 30° C. to about 150° C. and at a pressure from about 20 to about 250 psig. The duration of the contact step for these embodiments varies according to the reaction conditions, but can be approximately 16 hours.

In certain other embodiments, the method is performed as a continuous process, preferably in the vapor phase. Preferably, the halocarbon blend and a reducing agent are introduced into a heated reactor packed with a catalyst. In certain embodiments, a diluent, such as nitrogen gas, is utilized.

Other details concerning preferred conversion conditions in accordance with the present invention are provided in the Example section below.

According to another embodiment of the present invention, provided is a method of producing a hydrofluorocarbon comprising the steps of: (a) providing a halocarbon blend comprising 1,3-dichloro-1,1,2,2,3-pentafluoropropane; and (b) contacting said blend with a reducing agent to produce at least one 3-carbon hydrofluorocarbon. Depending on the conditions employed, the 3-carbon hydrofluorocarbon comprises at least one hydrofluoropropane or hydrofluoropropene. Examples of hydrofluoropropanes include, but are not limited to, HFC-245cb, $CF_3CFHCH_3$, and the like. Examples of hydrofluoropropenes include, but are not limited to, HFO-1234yf, and the like. In certain embodiments, mixtures of two or more products are produced.

EXAMPLES

Example 1

This example demonstrates reduction in accordance with the present invention of a HCFC-225ca/cb blend with excess hydrogen. The preferred reaction temperature for batch type reactions is from about 30° C. to about 200° C., more preferably from about 40° C. to about 150° C., and even more preferably from about 40° C. to about 140° C. The preferred reaction temperature used in this example is from about 60° C. to about 70° C., specifically about 65° C. The preferred reaction pressure is from about 50 psi to about 250 psi, more preferably from about 100 psi to about 200 psi, and even more preferably from about 130 psi to about 170 psi. The preferred reaction pressure used in this example is 150 psi.

A clean dry autoclave (600 mL capacity) was charged with 100 g of KOAc (1.02 mol) and 0.5 g of 10% palladium on carbon granules. The reactor was evacuated, charged with 450 mL ethanol and 100 g of a HCFC-225ca/cb blend (0.49 mol) via vacuum transfer, and then pressurized with hydrogen (150 psi). The contents in the reactor were heated to a temperature of approximately 65° C. The contents were stirred while being maintained at that temperature and pressure for 16 hours.

The autoclave was then cooled and maintained at 50° C. The volatile materials (23 g) were collected from the reactor in a cold trap (−78° C.) and analyzed by GC. The composition of the collected materials was determined to be $CF_3CF_2CH_3$ (42%), $CF_3CFHCH_3$ (34%) and $ClCF_2CF_2CFHCl$ (225cb) (24%); no unreacted 225ca was present. GC analysis of pot residue indicated only unreacted 225cb and ethanol solvent.

Example 2

This example demonstrates the reduction of a HCFC-225ca/cb blend with excess hydrogen at 120° C.:

The reaction of Example 1 was repeated except that the reaction was conducted at 120° C. The volatile materials (44 g) collected in a cold trap were analyzed by GC and indicated the production of $CF_3CF=CH_2$ (HFC-1234yf) (10%), $CF_3CF_2CH_3$ (20%), $CF_3CFHCH_3$ (48%), HCFC-225cb (20%). GC of the pot residue indicated mainly the solvent ethanol and unreacted 225cb.

Example 3

This example demonstrates the reduction of a HCFC-225ca/cb blend with excess hydrogen at 40-45° C.:

The reaction of Example 1 was repeated except that the reaction was conducted at 40-45° C. The volatile materials (13 g) collected in a cold trap were analyzed by GC and indicated the production of $CF3CF=CH_2$ (HFC-1234yf) (2%), $CF_3CF_2CH_2Cl$ (52%); GC indicated almost all 225cb and ethanol in the pot residue.

Example 4

This example demonstrates the reduction of a HCFC-225ca/cb blend with ammonium formate at 100° C.:

A clean dry autoclave (600 mL capacity) was charged with 50 g HCFC-225ca/cb blend (0.247 mol), 1 g of tetrakis(triphenylphosphine) palladium ($Pd(PPh_3)_4$) (0.08 mol), 32 g of ammonium formate (0.48 mol), and 50 ml of tetrahydrofuran (THF) under a nitrogen purge. The reactor was sealed and heated to approximately 98-100° C. The reactor was maintained at that temperature while being stirring for 22 hours (the pressure at the end of the reaction was about 200 psi).

The autoclave was then cooled and maintained at 50° C. The volatile materials (23 g) were collected from the reactor in a cold trap (−78° C.) and analyzed by GC. The composition of the collected materials was determined to be $CF_3CF_2CH_2Cl$ (HCFC-235cb), $CF_3CF_2CH_3$ (HFC 245 cb) and unreacted HCFC-225cb in the ratio of 54:7:6. Residue in the reactor contained $CF_3CF_2CH_2Cl$ and unreacted HCFC-225cb in the ratio 9:14 besides the solvent (THF).

Example 5

This example demonstrates the vapor phase reduction of a HCFC-225ca/cb blend. For vapor phase reactions, the preferred reaction temperature is from about 90° C. to about 700° C., more preferably from about 100° C. to about 650° C., and even more preferably from about 100° C. to about 600° C. The preferred reaction temperature used in this example is from about 110° C. to about 130° C., specifically about 120° C. The preferred reaction pressure is from about 1 to about 2 atmospheres, which is about the reaction pressure used in this example.

The reactor used in this example was a 12' long, stainless steel tube with a ½" diameter that was heat traced with electrical heating tape. The reactor was packed with 20 cc of 1% Pd on 4-6 mesh carbon granules. The reactor was equipped with a −78° C. cold trap to collect gases exiting the reactor. The reactor was preheated and dried under a nitrogen flow.

Initial studies indicated <10% total conversion at <80° C. and about 30% conversion at about 120° C.

Nitrogen was introduced into the reactor as a diluent at a rate of 10 cc/min; hydrogen was fed into the reactor at a rate of 46 cc/min; and a HCFC 225ca/cb blend was fed into the reactor at a rate of 10.8 grams/hr. At 135° C., the total conversion of HCFC-225 isomers was about 48%, while the ratio of HCFC-225ca to HCFC-225cb in the product mixture was 3 to 49 indicating a high selectivity for 225ca reduction.

At 145° C.; with an HCFC-225ca/cb blend feed rate of 8.5 g/h; and a $H_2$ feed rate of 30 cc/min, the product gases were $CF_3CF_2CH_3$ (26.3%), $CF_3CF_2CH_2Cl$ (23.9%), HCFC-225ca (0.6%), HCFC-225cb (48.5%), and 0.7% unknown materials. The main products, $CF_3CF_2CH_3$ and $CF_3CF_2CH_2Cl$ are derived from HCFC-225ca. Thus, nearly all the HCFC-225ca was reduced while little or none of the HCFC-225cb was reduced.

Example 6

This example demonstrates the vapor phase reduction of HCFC-225ca over activated carbon:

A 24" long by 1" diameter Monel reactor was charged with 100 cc acid treated activated carbon. The catalyst was dried at 400° C. for 4 h, 500° C. for 2 h, and finally at 550° C. for ½ h under 100 SCCM (standard cubic centimeter per minute) of anhydrous $N_2$. The catalyst was then pretreated with 5 wt % of $H_2$ in $N_2$ for 2 h.

A 1 L cylinder wrapped with heat trace elements at its outer wall heated to and maintained at a temperature of 45° C. The cylinder was then charged with 500 cc of $CF_3CF_2CHCl_2$. The cylinder was attached to a preheater that was maintained at 350° C. The preheater was, in turn, connected to the Monel reactor.

Approximately 50 SCCM of the HCFC-225ca was passed through the preheater and into the reactor. Concurrently, approximately 20 SCCM of hydrogen was introduced into the $CF_3CF_2CHCl_2$ stream at a point immediately after the preheater. The reactor was kept at 500° C. The gases coming out of the reactor were analyzed by an on-line GC and GCMS. The products are identified as follows: $CF_3CF_2CH_2Cl$ (57%), $CF_3CF_2CH_3$ (31%), $CF_3CF=CH_2$ (9%), unidentified 3%. The conversion of the starting material was about 33%.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for selectively reducing a halocarbon blend comprising the steps of:
   (a) providing a halocarbon blend comprising 1,3-dichloro-1,1,2,2,3-pentafluoropropane and at least one other chlorine substituted C2-C4 halocarbon compound; and
   (b) contacting said blend with a reducing agent under conditions effective to reduce at least a substantial portion of said at least one other chlorine substituted C2-C4 halocarbon compound without reducing a substantial portion of said 1,3-dichloro-1,1,2,2,3-pentafluoropropane.

2. The method of claim 1 wherein said other chlorine substituted C2-C4 halocarbon compound comprises one or more dichloropentafluoropropane isomers other than 1,3-dichloro-1,1,2,2,3-pentafluoropropane.

3. The method of claim 2 wherein said other chlorine substituted C2-C4 halocarbon compound comprises 3,3-dichloro-1,1,1,2,2-pentafluoropropane.

4. The method of claim 2 wherein said contacting step produces a composition comprising one or more C3 halocarbons.

5. The method of claim 1 wherein said blend consists essentially of dichloropentafluoropropane isomers.

6. The method of claim 5 wherein said blend consists essentially of 1,3-dichloro-1,1,2,2,3-pentafluoropropane and 3,3-dichloro-1,1,1,2,2-pentafluoropropane.

7. The method of claim 6 wherein said blend consists essentially of from about 1 to about 99 weight percent of 3,3-dichloro-1,1,1,2,2-pentafluoropropane and from about 1 to about 99 weight percent of 1,3-dichloro-1,1,2,2,3-pentafluoropropane.

8. The method of claim 6 wherein said blend consists essentially of from about 40 to about 55 weight percent of 3,3-dichloro-1,1,1,2,2-pentafluoropropane and from about 45 to about 60 weight percent of 1,3-dichloro-1,1,2,2,3-pentafluoropropane.

9. The method of claim 6 wherein at least about 50% of said 3,3-dichloro-1,1,1,2,-pentafluoropropane is reduced in said contacting step.

10. The method of claim 1 wherein said at least one other chlorine substituted C2-C4 halocarbon compound comprises at least one C3 hydrochlorofluorocarbon and wherein said contacting step converts at least a portion of said at least one C3 hydrochlorofluorocarbon to a compound selected from the group consisting of C3 hydrofluorocarbons, C3 hydrochlorofluorocarbons, C3 hydrofluoroolefins, and combinations of these.

11. The method of claim 10 wherein said at least one compound produced from said converting step comprises a halogenated 3-carbon aliphatic compound.

12. The method of claim 10 wherein said at least one compound produced from sid converting step is selected from the group consisting of hydrochlorofluoropropanes, hydrofluoropropanes, hydrofluoropropenes, and mixtures thereof.

13. The method of claim 10 said at least one compound produced from said converting step is selected from the group consisting of 1,1,1,2,2-pentafluoropropane, 1,1,1,2-tetrafluoropropane, 2,3,3,3-tetrafluoro-1-propene, 3-chloro-1,1,1,2,2-pentafluoropropane.

14. The method of claim 10 wherein said at least one compound produced from said converting step comprises at least one C3 hydrofluorocarbon.

15. The method of claim 14 wherein said at least one C3 hydrofluorocarbon comprises at least one pentafluorinated C3 hydrofluorocarbon.

16. The method of claim 15 wherein said at least one pentafluorinated C3 hydrofluorocarbon comprises at least $CF_3CF_2CH_3$ (HFC-245cb).

17. The method of claim 15 wherein said at least one pentafluorinated C3 hydrofluorocarbon comprises at least $CF_3CF_2CH_3$ (HFC-245cb).

18. The method of claim 10 wherein said at least one compound produced from said convening step comprises at least one C3 hydrofluoroolefin.

19. The method of claim 18 wherein said at least one at least one C3 hydrofluoroolefin is selected from the group consisting of tri, tetra and penta-fluorinated C3 hydrofluoroolefins and combinations of these.

20. The method of claim 18 wherein said at least one C3 hydrofluoroolefin comprises at least $CF_3CF=CH_2$ (HFC-1234yf).

21. The method of claim 18 wherein said at least one C3 hydrofluoroolefin comprises at least $CF_3CF=CFH$ (HFC-1225 ye).

22. The method of claim 10 wherein said at least one compound produced from said converting step comprises at least one C3 hydrochlorofluorocarbon.

23. The method of claim 22 wherein said at least one C3 hydrochlorofluorocarbon is a compound of the formula $C_3F_5H_2Cl$.

24. The method of claim 22 wherein said compound of the formula $C_3F_5H_2Cl$ comprises $CF_3CF_2CH_2Cl$ (HCFC-235ca).

25. The method of claim 10 wherein said at least one compound produced from said converting step comprises at least one C3 hydrofluorocarbon of the formula $C_3F_4H_4$.

26. The method of claim 10 wherein said at least one compound produced from said converting step comprises at least $HCF_2CF_2CH_3$.

27. The method of claim 1 wherein said reducing agent is hydrogen.

28. The method of claim 27 wherein said contacting step occurs in the presence of a palladium on carbon catalyst.

29. The method of claim 1 wherein the reducing agent is ammonium formate.

30. The method of claim 29 wherein said contacting step occurs in the presence of a tetrakis (triphenylphosphine) palladium catalyst.

31. The method of claim 1 wherein said contacting step occurs at a temperature of from about 30 to about 150° C. and at a pressure of from about 20 to about 250 psig.

32. The method of claim 1 wherein said contacting step occurs in the vapor phase.

33. The method of claim 32 wherein said contacting step occurs at a temperature of from about 50° C. to about 550° C.

34. A method of producing a C3 hydrofluorocarbon comprising the steps of:
(a) providing a halocarbon blend comprising 1,3-dichloro-1,1,2,2,3-pentafluoropropane; and
(b) contacting said blend with a reducing agent to produce at least one 3-carbon hydrofluorocarbon, wherein said reducing agent is ammonium formate.

35. The method of claim 34 wherein said blend comprises a plurality of dichloropentafluoropropane isomers.

36. The method of claim 35 wherein said blend comprises 3,3-dichloro-1,1,1,2,2-pentafluoropropane.

37. The method of claim 35 wherein said blend consists essentially of 1,3-dichloro-1,1,2,2,3-pentafluoropropane and 3,3-dichloro-1,1,1,2,2-pentafluoropropane.

38. The method of claim 34 wherein said hydrofluorocarbons are selected from the group consisting of pentafluoropropanes, tetrafluoropropanes, tetrafluoropropenes, and mixtures thereof.

39. The method of claim 34 wherein said at least one 3-carbon hydrofluorocarbon is selected from the group consisting of 1,1,1,2,2-pentafluoropropane, 1,1,1,2-tetrafluoropropane, 2,3,3,3-tetrafluoro-1-propene, and mixtures thereof.

* * * * *